(12) United States Patent
Alric et al.

(10) Patent No.: US 10,939,882 B2
(45) Date of Patent: Mar. 9, 2021

(54) DENTAL BITE BLOCK FOR 2D IMAGING

(71) Applicant: TROPHY, Rochester, NY (US)

(72) Inventors: Stephane Alric, Paris (FR);
Anna-Sesilia Vlachomitrou, Paris (FR)

( * ) Notice: Subject to any disclaimer, the term of this patent is extended or adjusted under 35 U.S.C. 154(b) by 0 days.

(21) Appl. No.: 15/307,502

(22) PCT Filed: Dec. 23, 2014

(86) PCT No.: PCT/IB2014/003251
§ 371 (c)(1),
(2) Date: Oct. 28, 2016

(87) PCT Pub. No.: WO2015/198086
PCT Pub. Date: Dec. 30, 2015

(65) Prior Publication Data

US 2017/0105686 A1 Apr. 20, 2017

Related U.S. Application Data

(60) Provisional application No. 62/016,785, filed on Jun. 25, 2014.

(51) Int. Cl.
*A61B 6/14* (2006.01)
*A61B 6/03* (2006.01)
*A61B 6/04* (2006.01)
*A61B 8/08* (2006.01)
*A61B 6/00* (2006.01)

(52) U.S. Cl.
CPC .............. *A61B 6/145* (2013.01); *A61B 6/032* (2013.01); *A61B 6/04* (2013.01); *A61B 6/14* (2013.01); *A61B 8/0875* (2013.01); *A61B 6/488* (2013.01)

(58) Field of Classification Search
CPC ........... A61B 6/14; A61B 6/488; A61B 6/145; A61B 8/0875; A61B 6/032; A61B 6/04
USPC ...................................... 378/38–40, 204, 208
See application file for complete search history.

(56) References Cited

U.S. PATENT DOCUMENTS

| | | |
|---|---|---|
| 4,782,503 A | 11/1988 | Molitor et al. |
| 2006/0056582 A1* | 3/2006 | Stoeckl ................. A61B 6/145 378/38 |
| 2006/0227939 A1* | 10/2006 | Walker ..................... A61B 6/14 378/208 |
| 2011/0142197 A1 | 6/2011 | Walker et al. |

(Continued)

OTHER PUBLICATIONS

International Search Report, dated Jul. 30, 2015, International Application No. PCT/IB2014/003251, 4 pages.

*Primary Examiner* — Courtney D Thomas

(57) ABSTRACT

Dental radiographic imaging systems and/or methods for using the same can provide panoramic 2D dental radiographic images. Providing improved panoramic 2D image quality can depend on imaging a desired/selected focal trough, which is itself based on a correct positioning of the patient's head inside the panoramic dental imaging system. Exemplary dental radiographic imaging systems and/or methods for using the same can provide a patient positioning device (e.g., bite stick embodiments) that can position or urge patients to get the right positioning (such as head tilt) to increase probabilities of the improved/best panoramic image reconstruction. Further, certain exemplary bite stick embodiments can repeatedly, consistently and/or correctly position patient after patient for panoramic imaging.

2 Claims, 10 Drawing Sheets

(56) References Cited

U.S. PATENT DOCUMENTS

2014/0147803 A1* 5/2014 Lecuyer .................. A61B 6/14
433/29

* cited by examiner

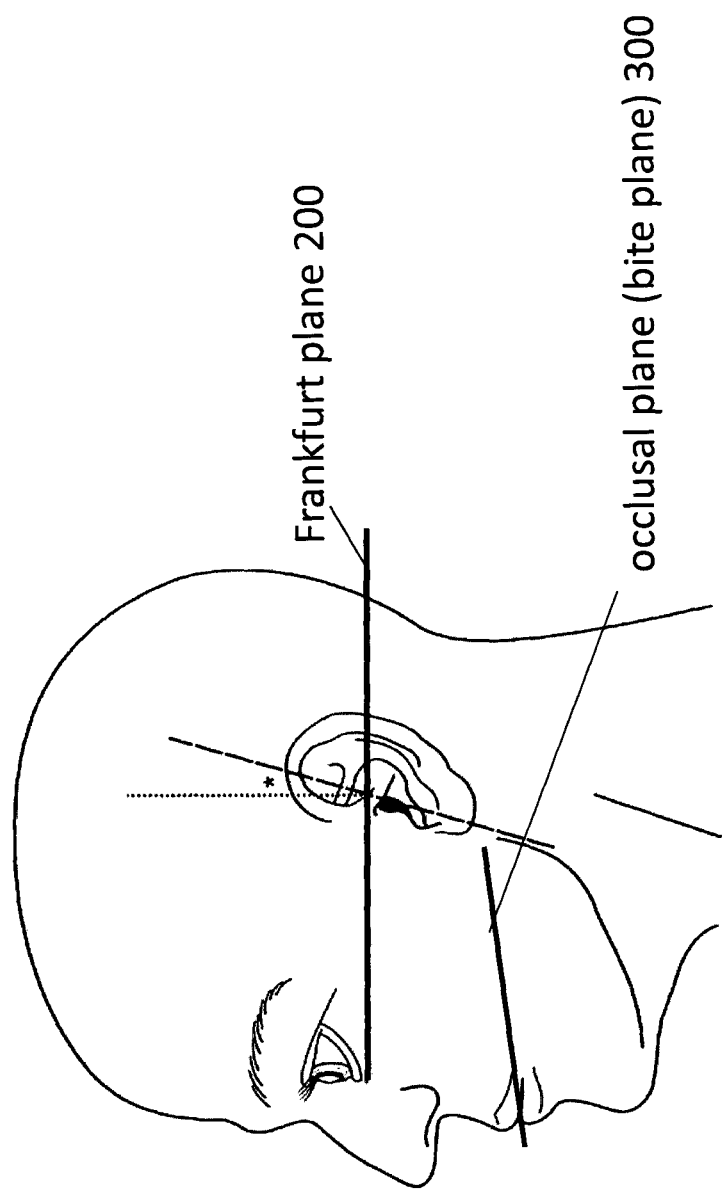

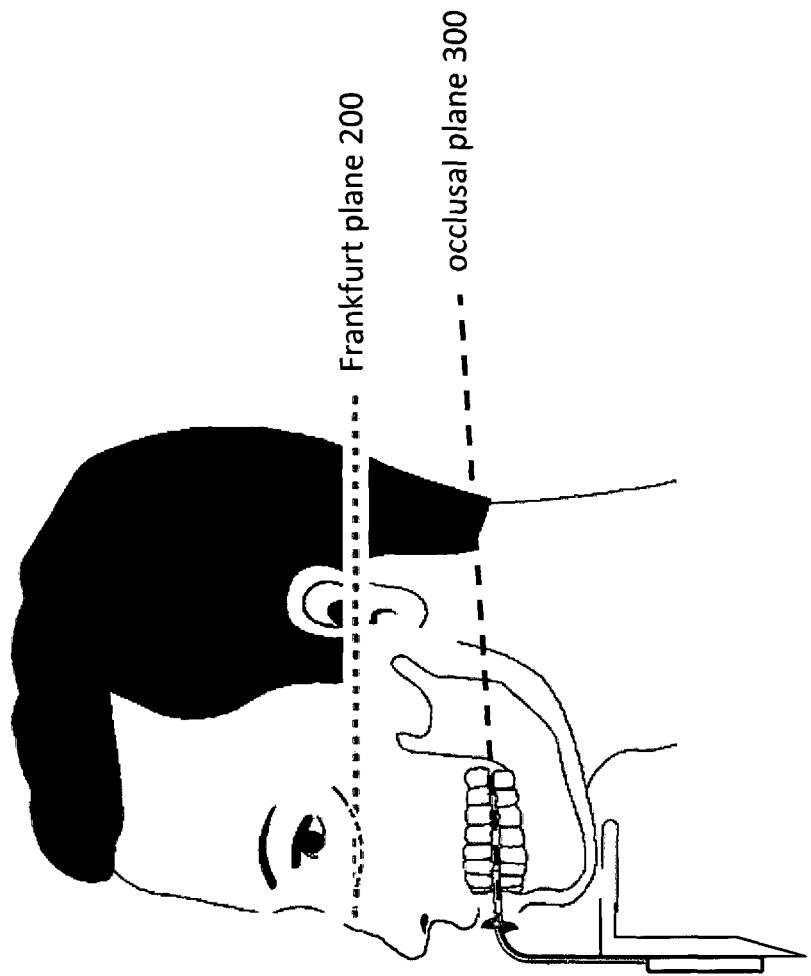
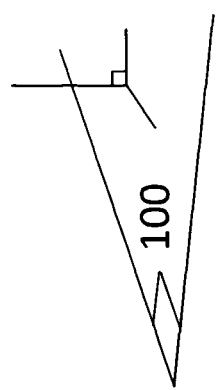
Fig. 7

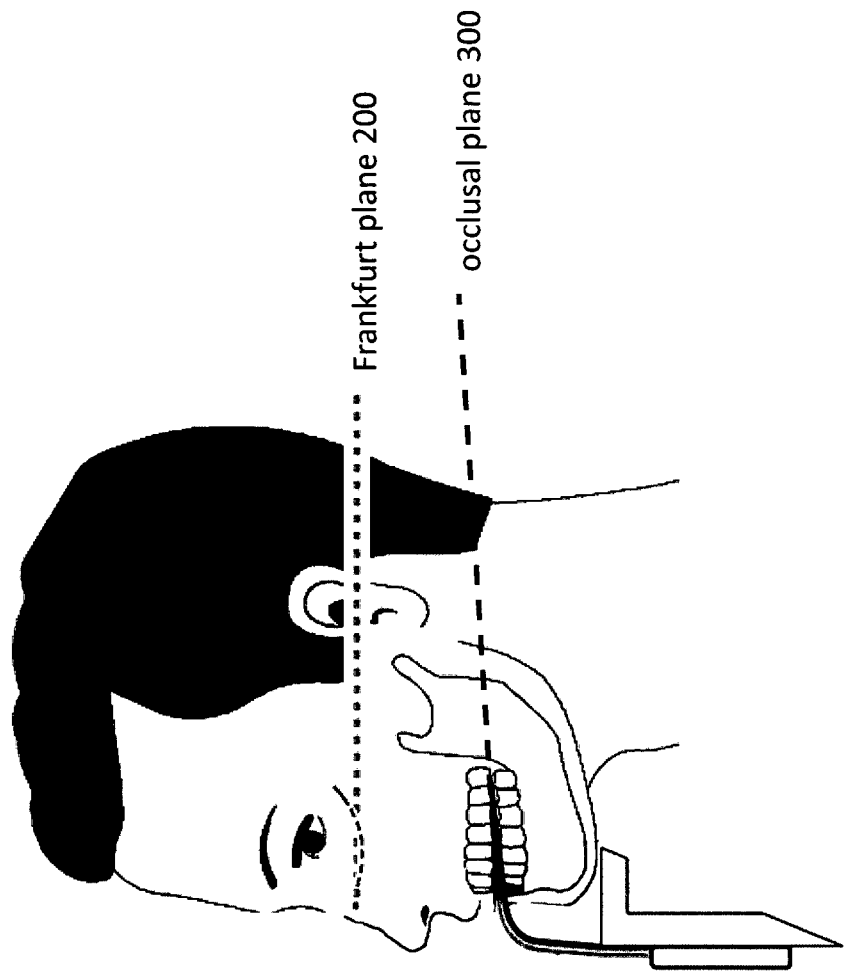
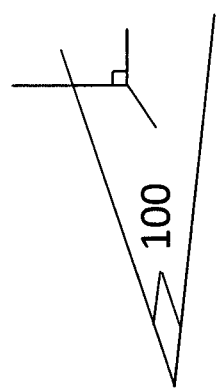
Fig. 8

DENTAL BITE BLOCK FOR 2D IMAGING

CROSS REFERENCE TO RELATED APPLICATIONS

This application claims the benefit of and is a U.S. National Phase filing of PCT Application PCT/IB2014/003251 filed Dec. 23, 2014 entitled "DENTAL BITE BLOCK FOR 2D IMAGING", in the name of Alric et al, which claims benefit of U.S. Provisional application U.S. Ser. No. 62/016,785, provisionally filed on Jun. 14, 2014, entitled DENTAL BITE BLOCK FOR 2D IMAGING", in the name of Alric et al, all of which are incorporated herein in their entirety.

FIELD OF THE INVENTION

The invention relates generally to the field of medical x-ray imaging, and more particularly, dental imaging apparatus and/or methods for correct positioning for dental panoramic X-ray imaging.

BACKGROUND

A panoramic dental imaging apparatus and/or methods can include a vertical column that supports a horizontal mount. A rotatable gantry with an x-ray source and a sensor disposed face to face on each of its extremities hangs below the horizontal mount. The gantry is able to rotate and translate in a horizontal plane with the patient positioned between the source and the sensor. A collimator is positioned in front of the x-ray source to shape an elongated x-ray beam.

During the panoramic imaging process, the x-ray source successively radiates x-ray towards overlapping regions of the dental arch and the radiation that has passed through the patient's teeth impinges the sensor. During the panoramic scanning, the gantry both translates and rotates and the source and sensor (e.g., at both extremities) can achieve a predetermined kinematic. A plurality of two dimensional (2D) images of the overlapping region are collected. At the end of the panoramic scan, a two-dimensional panoramic image of the whole dental arches can be reconstructed by merging the plurality of images.

Traditionally, the patient's head is fixed in position relative to the device for taking a panoramic radiograph by use of a patient's head positioner including a forehead pad and/or ear pads, a bite block, a nasion, or a chin pad. The necessary alignment of the head is usually achieved with the aid of optical lines projected onto the patient's head and depicting the Frankfort plane (Frankfurt plane or Francfort plane). For a correct patient's positioning allowing a good image quality, the Frankfort horizontal plane containing a straight line passing though the bottom of the eye socket and the ear canal must be horizontal.

The position of the occlusal plane is not directly registered but only indirectly by way of the Frankfort horizontal plane. To this end, the Frankfort horizontal plane projected onto the patient's head by the panoramic X-ray device and the incisal teeth in the edge-to-edge bite are used to derive the position of the occlusal plane. The correlation between the occlusal plane and the Frankfort horizontal plane is generally acknowledged from an anatomical standpoint, but positioning errors relative to the Frankfort horizontal plane of the patient cannot be excluded.

It can be appreciated that there is still a need for positioning apparatus and/or methods for panoramic imaging that can provide a cheaper, repeatable, consistent, and/or accurate positioning in an imaging area of a dental panoramic imaging apparatus.

SUMMARY

An aspect of this application is to advance the art of medical digital radiography, particularly for dental panoramic applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to repeatable, consistent, and/or accurate positioning in an imaging area of a dental panoramic imaging apparatus.

Another advantage offered by apparatus and/or method embodiments of the application relates to patient support structures to provide a spatial relationship that comprises a 6° to 10° angle or a 7° to 8° angle between contacting surfaces of opposing occlusal teeth in the dental arch and a Frankfort plane of a patient.

Another advantage offered by apparatus and/or method embodiments of the application relates to consistent patient positioning of a Frankfort plane within an imaging area of an extra-oral dental radiographic imaging system including a panoramic imaging capability.

According to one aspect of the disclosure, there is provided INDEPENDENT METHOD CLAIM in paragraph form.

According to one aspect of the disclosure, there is provided a dental imaging apparatus that can include a movable mount comprising at least one of a radiation source and a digital imaging sensor; an actuator that is energizable to move the movable mount in a scan pattern about an imaging area; a computer in signal communication with the digital imaging sensor and configured to acquire one or more of two-dimensional images of the digital imaging sensor positioned relative to the radiation source for the scan pattern; and a patient support structure to provide a spatial relationship to the scan pattern, where the spatial relationship aligns an occlusal plane determined by the patient support structure in the imaging area, where the spatial relationship includes a 6° to 10° angle with a portion of the scan pattern of the movable mount.

According to one aspect of the disclosure, there is provided a method of positioning a subject for dental radiographic imaging that can include providing a bitable bite block including opposing surfaces, where the opposing surfaces are configured to form a prescribed angle comprised between 6° and 10° from a prescribed plane; positioning the opposing surfaces of the bitable bite block between at least some upper teeth and one or more lower teeth to align a Frankfort plane of a patient parallel to the prescribed plane.

These objects are given only by way of illustrative example, and such objects may be exemplary of one or more embodiments of the invention. Other desirable objectives and advantages inherently achieved by the invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting x-ray system components, for example, are not shown in the drawings in order to simplify description.

FIG. 3 is a diagram that shows an exemplary relationship between a Frankfort horizontal plane and an occlusal plane according to embodiments of the application.

FIG. 7 is a diagram that shows exemplary positioning support embodiments can allow the Frankfort horizontal plane to be parallel to the scanning plan.

FIG. 8 is a diagram that shows exemplary positioning support embodiments can allow the Frankfort horizontal plane to be parallel to the scanning plan.

DESCRIPTION OF EXEMPLARY EMBODIMENTS

Figure 1:
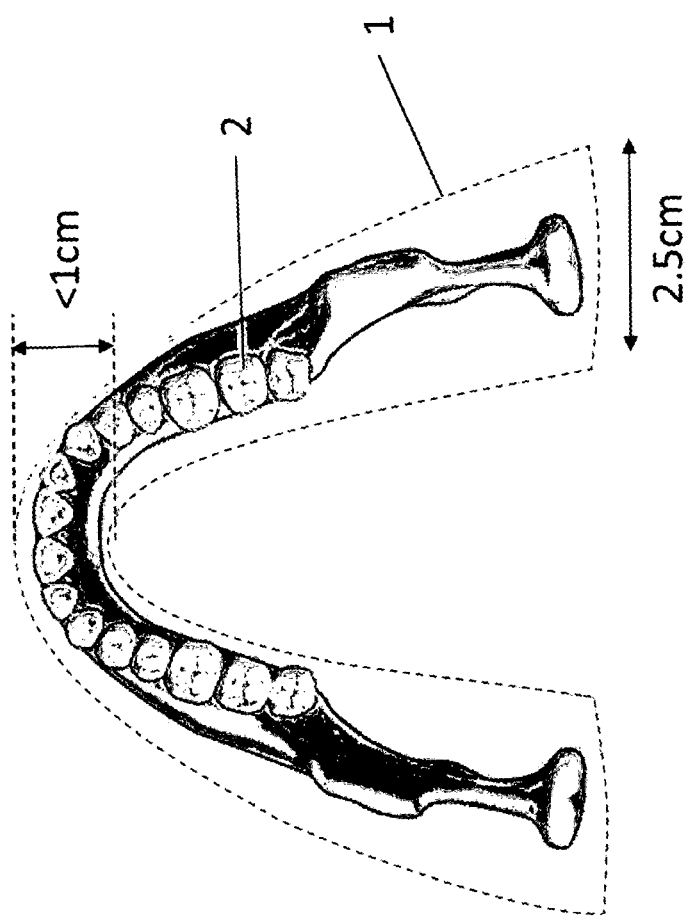
FIG. 1 is a diagram that shows a view of a focal trough (e.g., area of focus) during a panoramic scan illustrated with respect to lower jaw.

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Apparatus and/or method embodiments according to the application aim at facilitating a repeatable, accurate and rapid orientation of an occusal plane to the Frankfort plane for panoramic imaging.

FIG. 1 is a diagram that shows a focal trough during a panoramic scan illustrated with respect to top view of a lower jaw. As shown in FIG. 1, all the anatomic elements that are located inside a narrow zone of sharp focus 1, named the focal trough, are sharp on the panoramic image and anatomic elements located outside of the focal trough 1 are blurred. A panoramic image is then composed of sharp elements form the focal trough 1 superimposed on a kinetic blur. The position and thickness of the focal trough 1 depends on the kinematics (e.g., trajectory, linear and/or angular speed) of the gantry supporting the source and sensor (e.g., width of the sensor), as well as characteristics and configuration of any filtering devices (e.g., collimator) shaping the beam. In one example, a thickness of the focal trough can be 2.5 cm at the position of the molar and less than 1 cm at the position of the incisors.

Further, the focal trough 1 dimensions can be a tradeoff between precision data and amount of data. On one hand, there is a benefit need to have a focal trough thin enough to obtain precise information on the anatomical structure. On the other hand, an entire dental arch 2 should or preferably must be located inside the focal trough 1. Especially, each entire tooth including crown and roots should or preferably must be located entirely inside the focal trough 1, otherwise, some anatomical information can be lacking from the panoramic image.

For any exemplary kinetics of the gantry, the relative position of the teeth, and especially the incisors, and the dental arch, depends on the orientation of the head relative to the horizontal plane of the displacement of the x-ray source and the sensor. Especially, the angulation of the patient head may be critical for the presence of the roots of the incisors being inside the focal trough 1 and thus, shown in the panoramic image.

Figure 2C:
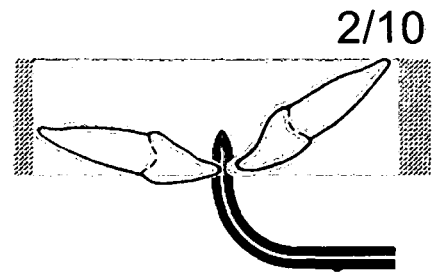
FIGS. 2a-2c are diagrams that respectively show a cross-section of the focal trough during a panoramic scan with respect to a paired teeth from the upper and lower jaw illustrating the root and crown of the paired teeth.
Figure 2B:
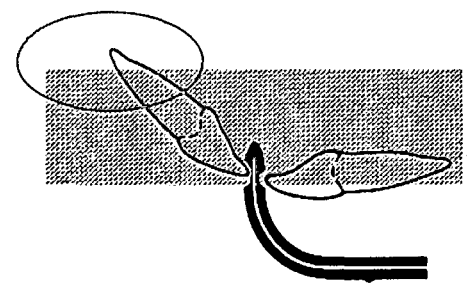
Figure 2A:
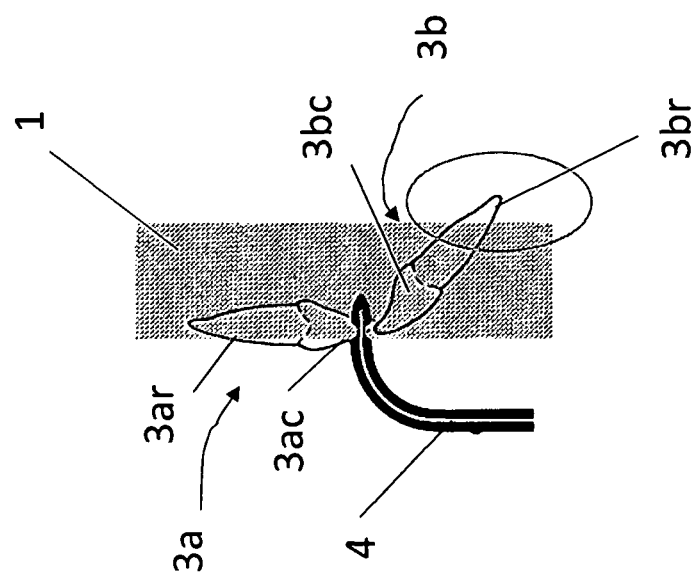

FIGS. 2a-2c are diagrams that respectively show a cross-section of the focal trough during a panoramic scan with respect to a paired teeth from the upper and lower jaw illustrating roots and crowns of the paired teeth. For example, as shown in FIGS. 2a-2c, the patient bites a bite stick 4 (bite block, bite wing, etc.) and the bite stick 4 is intended for patient's positioning, but the patient's head can rotate easily. When the patient's head is rotated forward relative to a correct position, the whole upper incisor 3a with its root 3ar and its crown 3ac is within the area of sharp focus 1, but the root 3br of a paired lower incisor 3b is out of the area of sharp focus 1. On the contrary and as shown in FIG. 2b, when the patient's head is too tilted is the rear direction, a whole lower incisor 3b with its root 3br and its crown 3bc lies inside the focal trough 1, but the root 3ar of the upper tooth 3a is out of the area of sharp focus 1. As shown in FIG. 2c, only a correct angular positioning of the patient's head allows the location of the whole upper incisor 3a and the paired lower incisor 3b to be in the area of sharp focus 1.

FIG. 3 is a diagram that shows a relationship between a Frankfort horizontal plane and an occusal plane according to exemplary embodiments of the application. In certain exemplary embodiments, the inventors determined that it appears that an improved angular position or the best angular position of the patient's head to have the full mouth series of teeth (and especially the incisors with their crowns and roots) inside the focal trough 1 is the position at which the Frankfort plane 200 of the patient is parallel to the plane of displacement (e.g., horizontal plane) of the source and sensor 100 or scanning plane 100. As shown in FIG. 3, the Frankfort horizontal plane 200 is the plane containing the ear canals and the bottom of the eye sockets. The Frankfort horizontal plane 200 can preferably form with the occlusal plane (or bite plane) 300, an angle in the range 6-10 degrees for a very large majority of patients. It is consequently desirable or necessary to provide a panoramic patient positioner or bite block that forces and/or ensures the position (e.g., consistently, repeatedly, accurately, etc.) the patient occlusal plane 300 to be at a 6-10° angle relative to the plane of motion of the x-ray source and sensor 100 or scanning plane 100, so that the Frankfort horizontal plane 200 lies parallel to (or within) to the Frankfort horizontal plane 200.

U.S. Pat. No. 7,497,619 discloses a bite block where bite piece surface forms a 15 degrees angle with the scanning plan. Such an angle is not appropriate to locate the incisors (as a whole, including the crown and the roots) in a thin focal trough, especially for focal trough smaller than 1 cm. There is consequently a need for a bite block/dental patient positioner and methods for using the same that can provide a correct (e.g., repeatable) angle between a bite stick (e.g., surface) and the scanning plane (or focal trough).

Additional exemplary advantages for using the Frankfurt horizontal plane exist. According to exemplary embodiments of the application, these can include but are not limited to, for example, panoramic imaging phantoms can be less visible in Frankfort horizontal plane so a global contrast of the panoramic image can be improved, increased or subjectively better when the patient is positioned in/based on the Frankfort horizontal plane.

Figure 4:
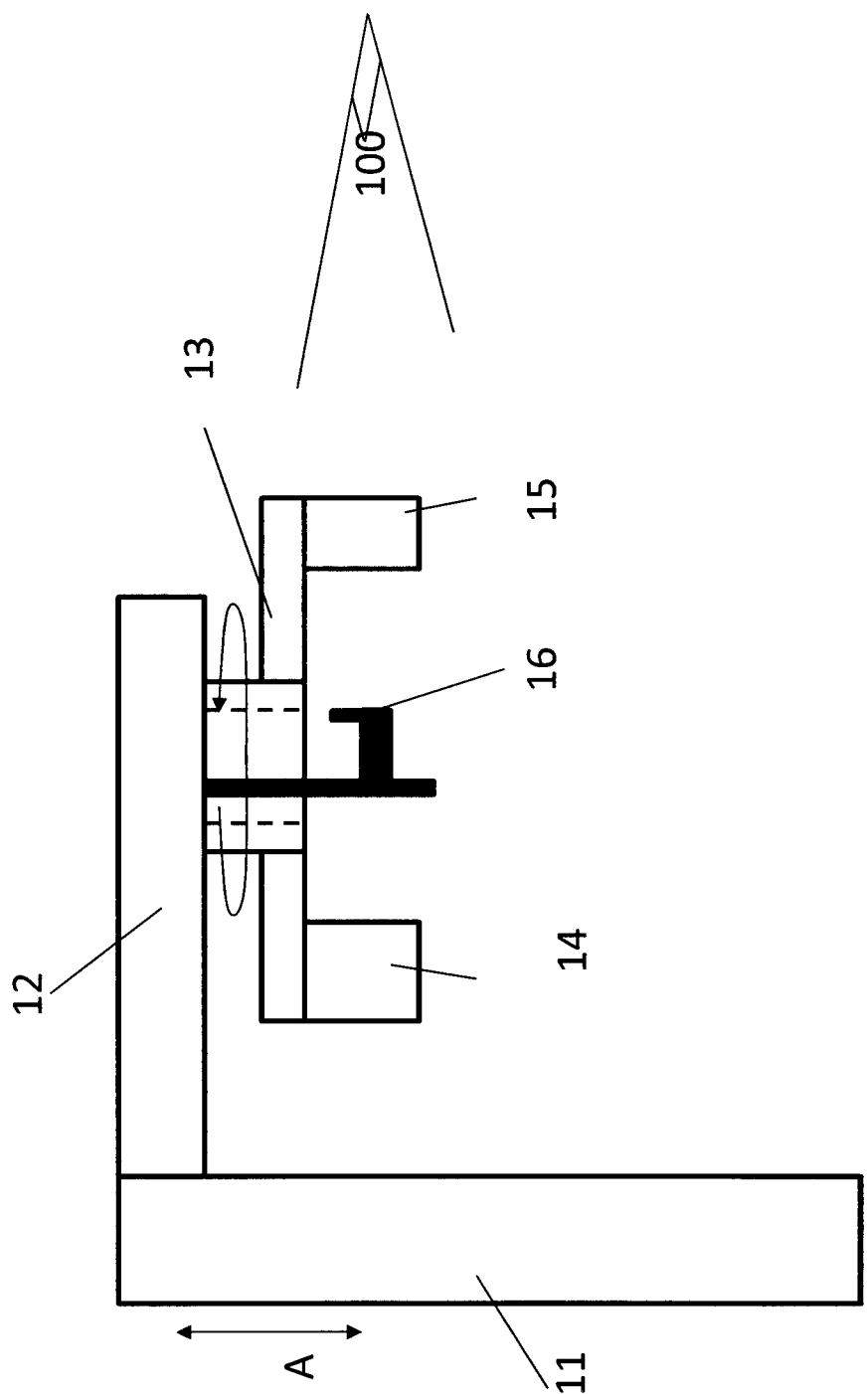
FIG. 4 is a diagram that shows an exemplary dental X-ray imaging panoramic apparatus that can use patient support embodiments and implement method embodiments for using the same according to the application.

FIG. 4 is a diagram that shows an exemplary dental X-ray imaging panoramic apparatus that can incorporate patient support embodiments and implement methods for using the same according to the application. As shown in FIG. 4, an exemplary dental X-ray imaging panoramic apparatus embodiment can include a support frame 11 (e.g., vertical frame) supporting a horizontal arm 12 and being able to adjust in one or more directions, for example, to the patient's height as illustrated by bi-directional arrow A. A rotatable gantry 13 can be coupled to or held by the horizontal arm 12 and can support in opposition (e.g., on each of its extremities), a sensor 14 and an x-ray source 15 facing each other. An actuator (not represented) can rotate and/or translate the gantry 13. During a panoramic scan, the source 15 and sensor 14 can follow a preset trajectory (2D/3D) that can in part or completely occur in a plane 100 (or parallel to) named the scanning plane (e.g., horizontal).

Figure 5:
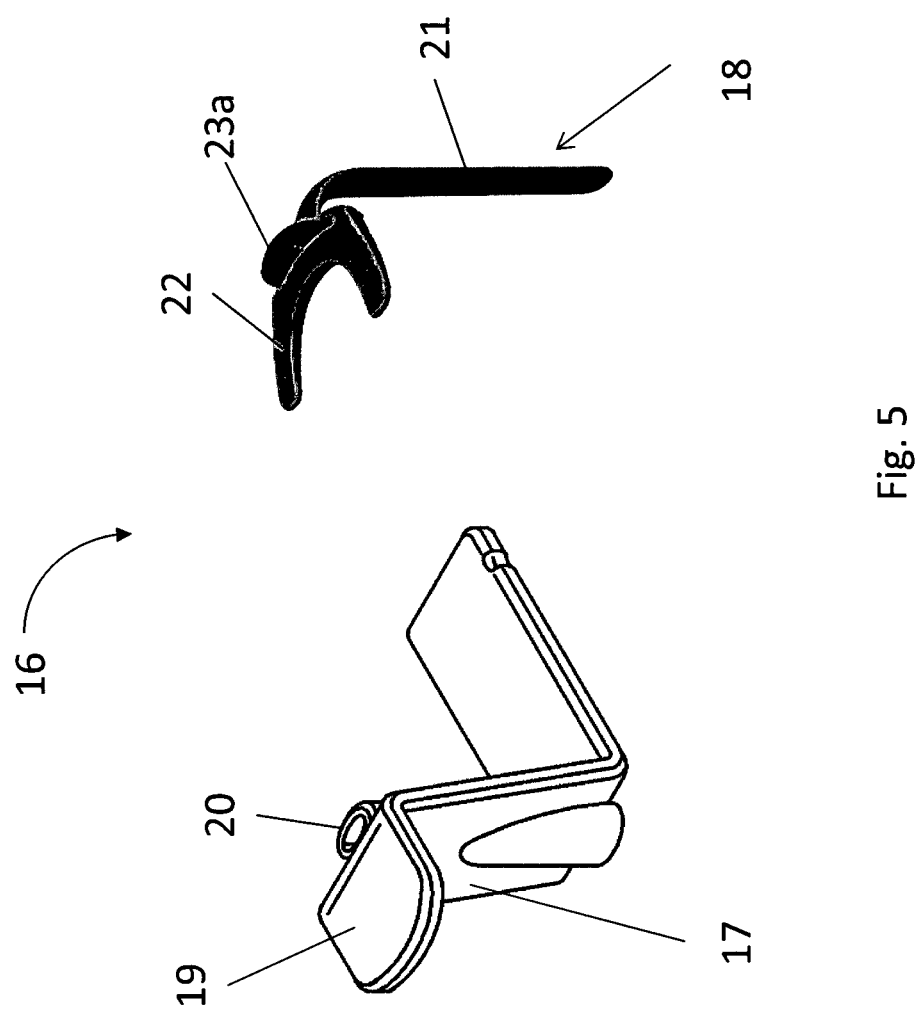
FIG. 5 is a diagram that shows an exemplary patient holder ensemble embodiment according to the application.

FIG. 5 is a diagram that shows a first exemplary patient holder ensemble embodiment according to the application. As shown in FIG. 5, an exemplary patient holder ensemble 16 embodiment can precisely position a patient between the source and the sensor. The patient holder ensemble 16 can include a chin rest 17 and a bite stick 18. The chin rest 17 includes a support surface 19 to support the patient's chin and a groove 20. The chin rest can be coupled to the rotatable gantry 13 or the horizontal arm 12 to position the patient with a prescribed position in the imaging area between the source 15 and sensor 14. The bite block 18 can include a shaft 21 that engages the groove 20 of the chin rest 17 and slides along the groove 20 to movably or reciprocally fix the bite stick 18 on the chin rest 17 (e.g., at various locations). The adjustment of the bite block 18 along the groove 20 can compensate for various patient heights. The bite stick 18 can also comprise a bite piece 22. This bite piece 22 can include a flat surface having a prescribed shape to match the mouth or dental arch (e.g., the general shape of a horse shoe, a "U" or in other words the shape of a dental arch). Preferably, a shape of the bite piece 22 can provide advantages such as a portion or a large part of the upper and lower dental arch is in contact with the bite piece, any tilt of the head of the patient can be reduced/ prevented, and/or occlusal plane or opposing occlusal tooth surfaces can contact or be guided by the bite piece 22. The bite piece, when fixed between the occlusal surfaces of the upper and lower teeth (e.g., bitten on) can correctly orient the occusal plane with reduced or eliminated error caused by front-to-back and/or side-to-side movement or the patient's head. In one exemplary embodiment, the bite piece 22 can be a solid hemisphere. In another exemplary embodiment, the bite piece 22 can have recesses or holes corresponding to some of the upper and/or lower teeth. In yet another exemplary embodiment, the bite piece 22 can have projections to align some of the upper and/or lower teeth. In certain exemplary embodiments, two (or more) flanges 23a and 23b can be respectively formed on an upper side and a lower side (e.g., each side or opposite sides) of the flat surface of the bite piece 22. The patient's front teeth (e.g., incisors, upper and lower, respectively) are leant against the flanges 23a and 23b to ensure a good positioning of the patient in the front-to-rear direction. In one embodiment, a buccal side surface of the incisors contacts a flat surface of the flanges 23a and 23b on the side of the bite piece 22, which can locate the incisors to a known selected position before an x-ray imaging scan or exposure.

Figure 6:
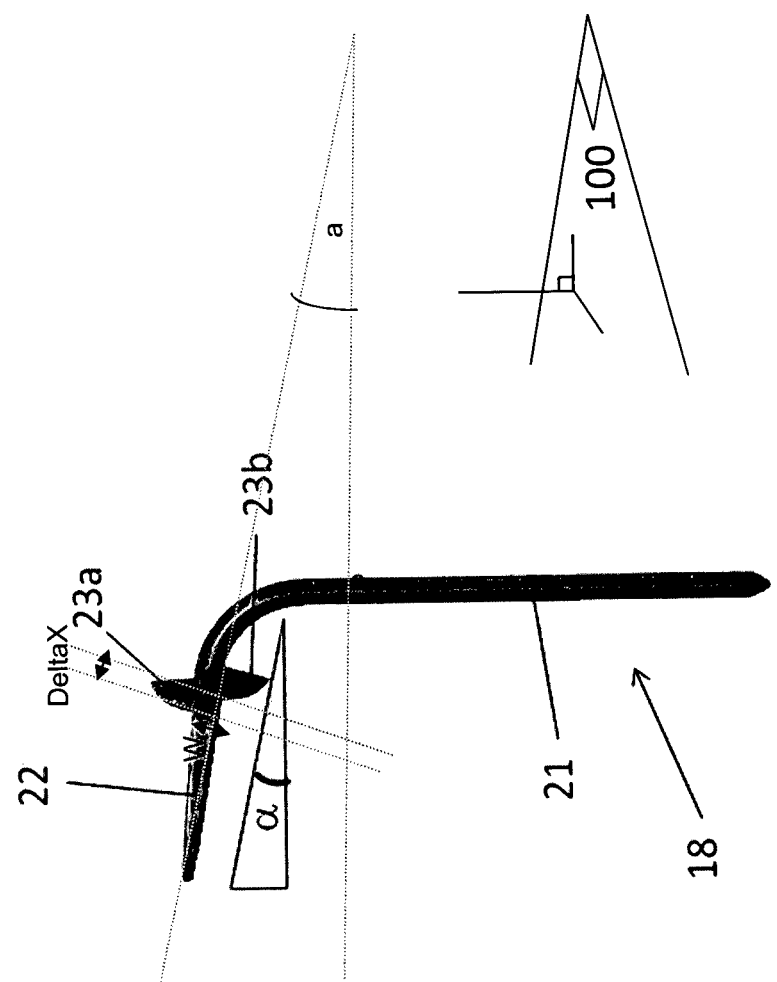
FIG. 6 is a diagram that shows exemplary incisor flanges and a relationship between a distance dimension between the bite (e.g., offset) of the upper and lower teeth (e.g., incisor(s)) and a width dimension between arms extending to contact an occusal surface between (e.g., molars) portions of the upper and lower jaw according to exemplary embodiments of the application.

FIG. 6 is a diagram that shows an exemplary incisor flange embodiment and a relationship between a distance dimension between the bite (e.g., offset) of the upper and lower teeth (e.g., incisor(s)) and a width dimension between arms of a bite piece extending to contact an occusal surface between (e.g., molars) portions of the upper and lower jaw according to exemplary embodiments of the application. In one exemplary embodiment, a distance dimension (e.g., horizontal distance) between the flanges 23a and 23b and a width dimension of our bite stick can be related. For example, upper and lower incisors bite should be on exactly the same focal trough and this shared focal trough can be defined by the horizontal distance set by the flange(s) 23a and 23b (e.g., between corresponding front or back surfaces) and/or sizes (e.g., width at the base or midpoint) of the flange(s) 23a and 23b themselves). In an x-ray projection image (e.g., used to form the panoramic image of teeth), the upper incisor(s) can be distinguished from the lower incisor (s). In one exemplary embodiment, such a projection image can be used to measure the distance dimension between the bite, which is used to define/determine the desired/minimum width of our bite stick 18 (or bite piece 22). As shown in FIG. 6, there can be a prescribed relationship between these parameters. In one embodiment, when DeltaX is the distance between flanges 23a and 23b, an angle (a°) of our bite stick to an horizontal plane and W the width of our bite stick, then DeltaX>=sin(a°)*W.

In one embodiment, the groove 20 of the chin rest 17 and the shaft 21 of the bite block 18 engaged inside the groove 20 are vertical and perpendicular to the scanning plane 100. The bite surface 22 can form with the shaft 21, an angle comprised between 96 degrees and 100 degrees. Consequently, when the shaft is inserted inside the vertical groove 20, the flat bite surface 22 can form with the horizontal scanning plane 100 an angle α comprised between 6 degrees and 10 degrees. As shown in FIG. 7, such exemplary embodiments can allow the Frankfort horizontal plane 200 to be parallel to the scanning plan 100. As shown in FIG. 8, such exemplary embodiments can allow the Frankfort horizontal plane 200 to be parallel to the scanning plan 100 while a positioning (e.g., 3D spatial position relative to the x-ray imaging scan) of the incisors (e.g., in the focal trough) can be controlled.

In certain exemplary embodiments, a value of the angle (e.g., angle α) between the bite surface 22 and the scanning plane 100 is preferably between 7 degrees and 8 degrees. In another exemplary embodiment, the angle value is preferably between 6 degrees and 8 degrees. In still another exemplary embodiment, the angle value is preferably between 8 degrees and 10 degrees.

Such exemplary bite block embodiments with a bite piece tilted with a 6-10 degrees angle relative to the Frankfort horizontal plane can allow/urge/force patient's head to reach and get positioned to an angle fitting with the correct alignment to the Frankfort horizontal plane. Such exemplary bite block embodiments with a bite piece tilted with a 6-10 degrees angle relative to the scanning plane can allow dental arch and/or localizations of the dental arch (e.g., the crown and root of the incisors) to be inside a focal trough having a thickness smaller than 10 mm. In one embodiment, dental cephalometric radiographic images can be taken.

Figure 9:
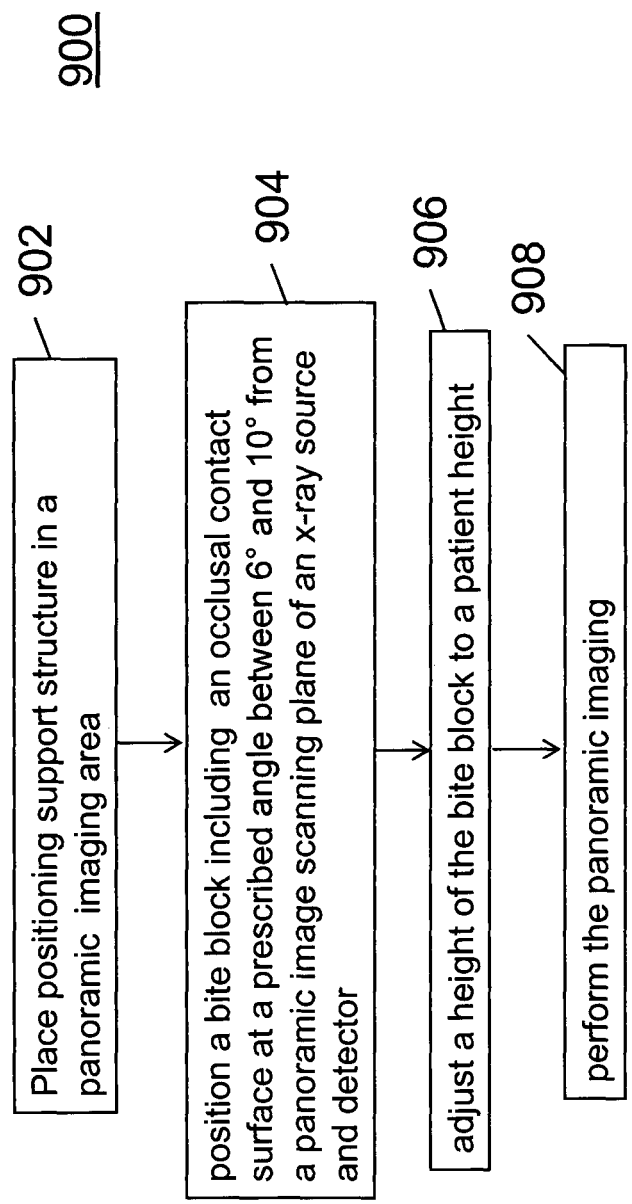
FIG. 9 is a flow chart that shows an exemplary method of generating a panoramic image using a dental extra-oral system according to embodiments of the application.

Referring to FIG. 9, a flow chart that shows an exemplary method of generating a panoramic image using a dental extra-oral system according to embodiments of the application will now be described. As shown in FIG. 9, the method can be implemented by embodiments of radiographic dental positioning support structures shown in FIGS. 5-8; however, the method of FIG. 9 is not intended to be limited thereby.

As shown in FIG. 9, a positioning support structure can be attached to or positioned in an imaging area of a dental extra-oral system (operation block 902). In one embodiment, a bite block can be attached to or adjusted along the positioning support structure in the imaging area. The bite block includes an occlusal contact surface at a prescribed angle between 6° and 10° from a panoramic image scanning plane of an x-ray source and detector of the system (operation block 904). Preferably, by placing occlusal surfaces of the mandibular and maxillary arches against opposing surface of the bite block, a dental arch can be placed in a focal trough while also positioning a Frankfort horizontal plane of a patient's head containing the dental arch parallel (e.g., horizontal) to the panoramic image scanning plane of an x-ray source and detector of the system. Optionally, a height of the bite block can be adjusted while the occlusal contact surface remains in the prescribed angle between 6° and 10° from a panoramic image scanning plane (operation block 906). At this point, a panoramic scan of the imaging area (e.g., dental arch) can be performed as known to one of ordinary skill in the art of panoramic imaging.

Figure 10:
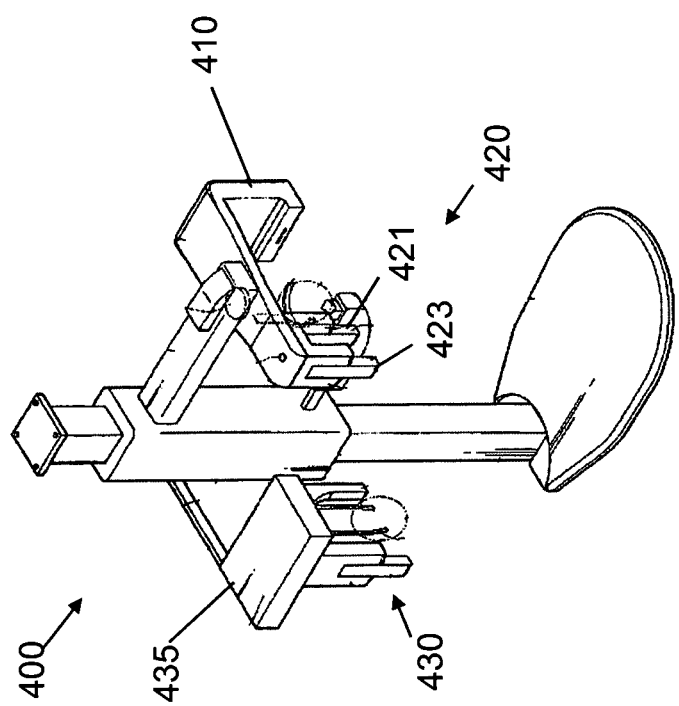
FIG. 10 is a diagram that shows an exemplary dental X-ray imaging panoramic apparatus that can use patient support embodiments and implement method embodiments for using the same according to the application.

Other exemplary dental imaging systems can combine one or more of CT, panoramic, and cephalometric imaging to form a single apparatus. FIG. 10 shows an exemplary dental CT, panoramic, and cephalometric imaging system. As shown in FIG. 10, a patient or other subject is positioned between an x-ray source part 410 and an x-ray sensor part 420 in a system 400. Either a CT sensor 423 and/or a panoramic sensor 421 can be positioned for obtaining/performing an exposure for CT imaging or panoramic imaging, respectively. As shown in FIG. 10, the combined panoramic, CT, and cephalometric imaging system 400 can include or remove a separate cephalometric imaging part 430 mounted at a separate arm 435. Separate patient positioners can be used (or duplicated) for each imaging mode, or shared between at least two imaging modes. Certain exemplary apparatus and/or method embodiments described herein can be applicable to positioners used for one or more imaging modes shown in FIG. 9.

In one exemplary embodiment, a dental imaging apparatus configured to obtain a panoramic radiographic image of at least a portion of a dental arch can include a movable mount that can include at least one of a radiation source and a digital imaging sensor; an actuator that is energizable to move the movable mount in a predetermined three-dimensional scan pattern; a computer in signal communication with the digital imaging sensor and configured to acquire one or more of two-dimensional images of the digital imaging sensor in the scan pattern; and a bite stick to provide a spatial relationship that comprises a 6° to 10° angle between contacting surfaces of opposing occlusal teeth in the dental arch and a Frankfort horizontal plane of a patient.

In one embodiment, a patient positioning structure or a bite piece thereof is preferably equipped with a replaceable protective sheath for hygienic reasons. Alternatively, the can be in the form of a replaceable bite piece. In one embodiment, the patient positioning structure can include a bite wing or a bitable shape or a flat shape corresponding to the dental arch or occlusal surfaces of the upper and/or lower jaw (e.g., solid or elongated arms with a gap therebetween). The patient positioning structure is preferably composed of a hard material, particularly a substantially radiolucent material. In one embodiment, patient positioning structure preferably occupies an angular range of a mandibular arch, which is between 20° and 40°, which can substantially reduce or prevents any sideways tipping or tilting of the patient's head. In one embodiment, the patient positioning structure has on its upper surface and on its undersurface a bite groove to accommodate part of the dental arch of the patient's upper and lower jaw respectively. In one embodiment, the patient positioning structure can include sensors to determine when a bite stick is firmly pressed between occusal surfaces of the mandibular and maxillary arches. An audible alert or visual indication can identify the selected tension/force.

Certain exemplary bite block embodiments use a fixed bite piece selectively tilted with a 6-10 degrees angle relative to the scanning plane so that the dental arch or localizations thereof can be inside a focal trough. Thus, one exemplary embodiment can have a fixed bite piece selectively tilted at 8 degrees angle relative to the scanning plane. However, selected individuals or patients can have a Frankfort plane between 6-10 degrees angle relative to the scanning plane. Accordingly, some exemplary embodiments can have a set of fixed bite pieces selectively tilted at 6, 7, 8, 9, and 10 degree angles, respectively, relative to the scanning plane. In one embodiment, an x-ray scout image or pre-shoot exposure can be performed before the dental imaging exposure (e.g., panoramic imaging). The x-ray scout view can be used with imaging applications known to one skilled in the art to locate physical features of the patient that can be used to determine an angle between the Frankfort plane and the occlusal plane for a given patient. Then, the dentist can use the identified or preferred bite piece of the set of fixed bite pieces selectively tilted at 6, 7, 8, 9, and 10 degree angles (according to the x-ray scout image or pre-shoot exposure of the given patient) for a subsequent dental imaging exposure (e.g., panoramic scan).

Exemplary applications of apparatus and/or method embodiments herein were described with respect to panoramic imaging of the teeth, however, embodiments of the application are not intended to be so limited, for example additional applications of described embodiments can include but are not limited to medical fields, NDT fields, and/or applications including orthodontics, periodontics, endodontics, prosthodontics, oral and maxillofacial surgery, or pediatric dentistry. Certain exemplary apparatus and/or method embodiments according to the application can be used for dental imaging apparatus including at least one of a panoramic dental imaging apparatus, a combined dental imaging apparatus including a panoramic dental imaging device and at least one of a computed tomography dental imaging device image, a cephalometric dental imaging device, an ultrasonic dental imaging device, or an ENT a radiographic imaging device.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A dental imaging apparatus for obtaining a radiographic image of an object, the apparatus comprising:
   a movable mount comprising at least one of a radiation source and a digital imaging sensor;
   an actuator that is energizable to move the movable mount in a scan pattern about an imaging area;
   a computer in signal communication with the digital imaging sensor and configured to acquire one or more of two-dimensional images of the digital imaging sensor positioned relative to the radiation source for the scan pattern; and
   a patient support structure to provide a spatial relationship to the scan pattern, where the spatial relationship aligns an occlusal plane determined by the patient support structure in the imaging area, where the spatial relationship comprises a 6° to 10° angle with a scanning plane of the scan pattern of the movable mount, and
   where the patient support structure comprises a chin rest, where the chin rest is connected to the dental imaging apparatus with a prescribed relationship to the movable mount;
   where the patient support structure further comprises a set of fixed bite pieces selectively tilted in a range of 7-8 degree angles for a subsequent dental imaging exposure, and
   where the patient support structure that is configured to couple to the set of fixed bite pieces is not pivotable.

2. A dental imaging apparatus for obtaining a radiographic image of an object, the apparatus comprising:
   a movable mount comprising at least one of a radiation source and a digital imaging sensor;
   an actuator that is energizable to move the movable mount in a scan pattern about an imaging area;
   a computer in signal communication with the digital imaging sensor and configured to acquire one or more of two-dimensional images of the digital imaging sensor positioned relative to the radiation source for the scan pattern; and
   a patient support structure to provide a spatial relationship to the scan pattern, where the spatial relationship aligns an occlusal plane determined by the patient support structure in the imaging area, where the spatial relationship comprises a 6° to 10° angle with a scanning plane of the scan pattern of the movable mount, and
   where the patient support structure comprises a set of at least one fixed, rigid bite pieces selectively tilted in a range of 7-8 degree angles for a subsequent dental imaging exposure, and where the patient support structure that is configured to couple to the set of fixed, rigid bite pieces is not pivotable.

* * * * *